United States Patent
Scott

(10) Patent No.: US 7,632,848 B1
(45) Date of Patent: Dec. 15, 2009

(54) MEDICAL TREATMENT OF MUSCLES BY EXPOSURE TO ANESTHETIC DRUGS

(76) Inventor: Alan Brown Scott, 37 Avon Ave., Mill Valley, CA (US) 94941

(*) Notice: Subject to any disclaimer, the term of this patent is extended or adjusted under 35 U.S.C. 154(b) by 209 days.

(21) Appl. No.: 11/867,532

(22) Filed: Oct. 4, 2007

(51) Int. Cl.
*A61K 31/445* (2006.01)
(52) U.S. Cl. ....................................................... 514/317
(58) Field of Classification Search ................... 514/317
See application file for complete search history.

(56) References Cited

U.S. PATENT DOCUMENTS

2004/0058313 A1* 3/2004 Abreu ........................... 435/5

* cited by examiner

*Primary Examiner*—Raymond J Henley, III

(57) ABSTRACT

According to one aspect, the fibers of a relatively weak muscle to be strengthened are exposed to a local anesthetic drug such as bupivacaine. The concentration and volume of the local anesthetic drug are sufficient to causes the muscle to enlarge and become stronger. In one embodiment, the increased strength of the treated muscle improved the position and the movement of the eye to which it was attached. The local anesthetic drug may be injected into the fibers of the muscle or infused around the muscle.

9 Claims, No Drawings

MEDICAL TREATMENT OF MUSCLES BY EXPOSURE TO ANESTHETIC DRUGS

FEDERALLY SPONSORED RESEARCH

Not Applicable

SEQUENCE LISTING OR PROGRAM

Not Applicable

BACKGROUND

1. Field

This relates to the medical treatment of skeletal (striated) muscle disorders, specifically a method for strengthening and thereby improving the function of such muscles.

2. Prior Art

Many medical conditions are the result of muscles that function improperly. One example is the controlling muscles of eyes. When the strength of the controlling muscles is unequal, the eyes become crossed or misaligned. Another example is that of the extensor muscles of an arm that is held in a flexed position after a stroke of the brain; because such muscles lack proper brain control they are under-active and become weak. Yet another example is that of weakness of a muscle due to atrophy during a period when the nerve to the muscle was temporarily damaged.

Prior Methods of Treatment for Strengthening Muscles

Various methods of strengthening improperly functioning muscles exist. The following are some of these methods.

1. Physical therapy and active exercise to move the limb, activate the attached muscles, and increase the amount of muscle (hypertrophy) is a well-established approach. This method is generally safe, but it is time-consuming, often extending over many weeks or months. It is uncomfortable as the muscle must pull against resistance to gain strength; "no pain, no gain" is a byword of this method. The method is not applicable to many muscles such as those of the eye and the larynx because these muscles are deep in the body so that there is no way to create resistance to the movement as can be done with weights, springs, or the pull of gravity with muscles attached to the limbs or the torso of the body.

2. Surgical lengthening or shortening of a muscle or its tendon to tighten or loosen tension is an important method of treatment. It is invasive, painful, carries risks as with all surgery, and requires hospitalization for all but the simplest procedures. The method is not hypertrophic, i.e., it does not strengthen the muscle by increasing the number and size of muscle fibers.

3. Botulinum toxin injection into a muscle blocks nerve transmission to the muscle. This can relax overactive muscles, allowing their antagonist muscles to shorten. However, this method does nothing to directly strengthen or enlarge the antagonist muscles.

4. Electrical stimulation through electrodes applied to the skin over the muscle can activate and strengthen weak muscles. This method is useful for limb muscles, but no embodiment of this approach can be used for small muscles such as those in the larynx or in the eye due to the depth of these muscles in the body.

5. Systemic drugs such as anabolic steroid hormones taken orally, together with exercise, will enlarge and strengthen muscles. However, such drugs are usually illegal and often dangerous to health. Furthermore, they are not selective enough to influence a single target muscle or muscles, as is frequently required in medical treatment.

Prior Basic Science Work with Local Anesthetics and Muscles

Of relevance here is the fact that anesthetic drugs are toxic to muscles. Muscles are made up of many protein units (sarcomeres) strung together like the railway cars on a train. Within minutes after exposure to the local anesthetic drug bupivacaine there is breakdown of the connections between these sarcomere units, resulting in irreversible breakdown of the muscle fibers. Sokoll et al. first demonstrated this toxicity to fibers of striated skeletal muscles from exposure to the anesthetic drug bupivacaine. (Sokoll M D, Sonesson B, and Thesleff S., 1968, Denervation changes produced in an innervated skeletal muscle by long-continued treatment with a local anesthetic, Euro J of Pharmacology, 4 (2), pp. 179-187).

Exposure to local anesthetic drugs and study of the resulting degeneration, repair, and regeneration has revealed that anesthetic drugs of both the amino-amide and aceto-amide classes have this toxic effect on muscle fibers. (Bradley W., 1979 Muscle fiber splitting, Muscle Regeneration (pp. 215-232), New York: Raven Press; Hall-Craggs, E. C., 1974, Rapid Degeneration and regeneration of whole skeletal muscle following treatment with bupivacaine (Marcain), Experimental Neurology, 43, 349-358; Hall-Craggs E. C. & Seyan, H. S., 1975 Histochemical changes in innervated and denervated skeletal muscle fibers following treatment with bupivacaine (marcain), Exp. Neurol, 46 (2), 345-354; Libelius, R., Sonesson, B, Stamenovic B. A., and Thesleff, S. 1970 Denervation-like changes in skeletal muscle after treatment with local anaesthetic (Marcaine), J. Anat. 106 (2), 297-309).

Damaged muscles fibers are not repaired but are removed and replaced. (Benoit, P. W., & Belt, W. D., 1970, Destruction and regeneration of skeletal muscle after treatment with a local anaesthetic, bupivacaine (Marcaine). J. Anat, 107 (Pt 3), 547-556).

However, the basic cell membrane, the nerve supply, and the nearby satellite cells remain intact after initial exposure. Within hours of exposure to bupivacaine, inflammatory cells are found in the affected area; these act to clear away the dead muscle fibers. Within one or two days, satellite cells—cells that normally lie dormant within the muscle—begin to proliferate and they regenerate the muscle fibers over the next 7 to 14 days. (Hall-Craggs E. C. B., 1980, Survival of satellite cells following exposure to the local anesthetic bupivacaine (Marcaine), Cell Tissue Res., 209, 131-135; Hall-Craggs E. C. B., 1980, Early ultrastructural changes in skeletal muscle exposed to the local anaesthetic bupivacaine (Marcaine). Br, J. Exp. Path 61, 139-149; Carlson, B. M., Shepard, B., and Komorowski, T. E., 1980 A histological study of local anesthetic-induced muscle degeneration and regeneration in the monkey, J. Orthop. Res., 8 (4): 485-494; Nonaka I., Takagi A., Ishiura, S., Nakase, H. & Sugita, H., 1983, Pathophysiology of muscle fiber necrosis induced by bupivacaine hydrochloride (Marcaine). Acta Neuropathol. (Berl.), 60 (3-4), 167-174; Schultz, E., Jaryszak, D. L., 1985 Effects of skeletal muscle regeneration on the proliferation potential of satellite cells, Mech. Ageing Devel. 30, 63-72; McLoon, L. K., Nguyen, L. T., Wirtschafter, J., 1998, Time course of the regenerative response in bupivacaine injured obicularis oculi muscle. Cell Tissue Res. 294, 439-447).

Several investigators have suggested the use or studied the application of bupivacaine and other anesthetic drugs as treatment to weaken over-active muscles by virtue of their damaging effect. (Park, C. M., Park, S. E., Oh, S. Y., 2004 Acute effects of bupivacaine and ricin mAb35 on extraocular muscle in the rabbit. Curr. Eye Res., 29, 293-301; McLoon, L. K., & Wirtschafter, J. 1993, Regional differences in subacute response of rabbit orbicularis oculi to bupivacaine-induced myotoxicity as quantified with a neural cell adhesion molecule immunohistochemical marker. IOVS 34 (12) 3450-3458.).

U.S. Pat. No. 5,096,930 to Zenka et al., Issued Mar. 17, 1992, specifies use of n-butlyamine, a compound without known anesthetic properties, to aid regeneration of injured muscle. However, as far as I am aware, this method will not strengthen normal muscles.

Three authors have shown that bupivacaine injection in sufficient concentration and volume into the extensor digitorum longus, a muscle in the hind limb of the rat, is followed by enlargement of the muscle beyond its original size. (Rosenblatt, J. D., 1992, A time course study of the isometric contractile properties of rat extensor digitorum longus muscle injected with bupivacaine, Comp. Biochem. Physiol., 101 (2), 361-367; Rosenblatt, J. D., Woods, R. I., 1992, Hypertrophy of rat extensor digitorum longus muscle injected with bupivacaine. A sequential histochemical, immunohistochemical, histological, and morphometric study, J. Anat., 181, 11-27; Plant, D. R., Beitzel, F., & Lynch, G. S., 2005, Length-tension relationships are altered in regenerating muscles of the rat after bupivacaine injection, J. Appl. Physiol., 98 (6), 1998-2003).

In these papers the authors discuss how they measured muscle strength and emphasized that the muscle did not grow stronger, but maintained its original strength as it enlarged.

Local Anesthetics and Eye Muscle Problems

Beginning about 1980, changes were made by a majority of eye surgeons in the US in the technique of inducing anesthesia (blocking pain nerves) and akinesia (blocking the motor nerves to eye muscles to reduce movement) in preparation for cataract surgery. Since those changes were instituted, various eye muscle problems were encountered. Most notably, a misalignment (strabismus) of the injected eye was often seen a few days after the operation, something rarely encountered before. (Rainin, E. A., & Carlson, B. M., 1985 Postoperative diplopia and ptosis, A clinical hypothesis based on the myotoxicity of local anesthetics, Arch. Opthalmol., 103 (9), 1337-1339; Grimmett, M. R., Lambert, S. R., 1992 Superior rectus muscle overaction after cataract extraction, Am. J. Opthalmol., 114 (1), 72-80; Munoz, M., 1994, Inferior rectus muscle overaction after cataract extraction, Am. J. Opthalmol., 118 (5), 664-6.).

The first change made by the eye surgeons was placement of the anesthetic injection alongside the eye (peri-bulbar) instead of behind the eye (retro-bulbar) as was formerly done. The eye muscles are in this peribulbar region and are thus susceptible to exposure to the anesthetic.

The second change was an increase in the volume of the injection from 1.5-2.0 ml to 4.0-7.0 ml to deepen and prolong the anesthesia. It was found that the chance of inducing strabismus increased with increasing injection volume. (Goldchmit M, Scott A B. 1994. Avaliacao da motilidade extrinsca ocular de pacientes facectomizados sob anestesia retrobulbar, Arq. Bras. Oftal., 57, 114-116).

The third change was the use of the amino-amide anesthetic bupivacaine, either alone or added with other anesthetic drugs in the same syringe. Enlarged muscles were shown on magnetic resonance images in some of these cases. The specific pattern of change in the image of the enlarged muscle was interpreted as being fibrous tissue and scarring from the drug injected into the muscle rather than enlargement by growth of new muscle (hypertrophy). (Hamed, L. M. & Mancuso, A., 1991, Inferior rectus muscle contracture syndrome after retrobulbar anesthesia. Opthalmol., 98, 1506-1512.) The amount of the strabismus was often greater looking to the direction away from that of the action of the affected muscle, as if the affected muscle restrained movement. Clinical investigators consistently proposed some form of scarring or fibrosis to explain the altered movements of the injected eye. (Capo, H., Roth, E., Johnson, T., Munoz, M. & Siatkowski, R. M., 1996, Vertical strabismus after cataract surgery, Opthalmology 103 (6), 918-921; Rainin, E. A. & Carlson, B. M., 1985 Postoperative diplopia and ptosis. A clinical hypothesis based on the myotoxicity of local anesthetics. Arch. Opthalmol., 103 (9), 1337-1339; Carlson, B. M., Emerick, S., Komorowski, T. E., Rainin, E. A., Shepard, B. M., 1991, Extraocular Muscle Regeneration in Primates, Opthalmology 99 (4), 582-589.).

All authors have attributed the eye problems encountered (strabismus and muscle enlargement) to inflammation, scarring, fibrosis, and contracture (muscle shortening). No authors or physicians have ever mentioned or reported any increase in muscle strength from these changes. To the best of my knowledge, the deficiencies of the prior methods for muscle strengthening listed above have continued.

ADVANTAGES

Accordingly, in one or more aspects the present method for strengthening muscles has advantages over surgical treatment. For one, the method employs a simple injection in the office, with no need for expensive hospitalization and extended recovery. The material injected is an anesthetic, so that pain is minimal, and there is no pain following injection. The method has advantages over botulinum toxin injection in that the muscle exposed to local anesthetic drugs will recover its action within 7-10 days, whereas botulinum toxin requires the muscle to be paralyzed at least a month to have a good and lasting effect. During this time the patient is usually unable to use the paralyzed eye effectively. The method has been shown to have an effect lasting many months, whereas botulinum toxin often requires re-injection at more frequent intervals. Further advantages of one or more aspects will be come apparent from a consideration of the ensuing description and claims.

SUMMARY

According to one aspect, the fibers of a muscle are exposed to an adequate concentration and volume of a local anesthetic drug such as bupivacaine. This causes the muscle to enlarge and become stronger. In one embodiment, the increased strength of the treated muscle improved the position and the movement of the eye to which it was attached.

DESCRIPTION

Some patients have one or more muscles whose function is substandard, i.e., the muscle is relatively weak in operation and function, such that the skeletal component that the muscle is arranged to move does not function effectively or optimally. One obvious example is the eye muscle, which in some patients, especially children, is significantly weaker than its opposing muscle, such that the eyeball may be turned inwardly (esotropic) or outwardly (exotropic). In order to correct this condition, known as strabismus or cross-eye, it would be desirable to strengthen the weaker muscle. Another example is a muscle in the arm that controls a finger scarred by injury. Since the finger cannot function normally, the muscle becomes weak from disuse. After repair of the finger, it would be desirable to strengthen the weak muscle.

Such skeletal muscles vary greatly in size, in internal fiber type, and in accessibility to treatment. Muscles composed of rapidly contracting or "fast" fibers are most susceptible to the present method. Examples of such "fast" muscles are those moving the fingers and hands, the toes and feet, the vocal cords in the larynx, and the eyes in their orbits. I have found that purposeful exposure of these "fast" muscles to a local anesthetic drug will cause such muscle to strengthen as the repair and growth continues beyond replacement of the injured fibers to actual hypertrophy with increased strength.

Below are descriptions of two embodiments or examples of how a muscle may be exposed to an anesthetic drug to strengthen it.

EXAMPLE 1

In one embodiment, an eye muscle is selected for treatment. For an eye that is esotropic (turned inward or crossed), the physician will want to strengthen the lateral rectus muscle, which acts to pull the eye outward into better alignment. The surface of the eye is anesthetized with eye drops. A syringe is filled with up to 5.0 cc of bupivacaine, enough to fill the muscle and reach all the muscle fibers. The concentration of the bupivacaine solution is from 0.5% to 3.0%. The volume and concentration are varied depending on the amount of strengthening effect required. The syringe is attached to an injection needle insulated on its shaft. Therefore, the muscle electrical activity is picked up only with the exposed tip of the needle. The needle is attached to a wire leading to an electromyographic (EMG) recorder. A second wire leads to a ground attached to the skin of the patient's body. The eye is moved to a position at which the lateral rectus muscle to be treated is activated electrically as well as physically contracted. As the tip of the needle approaches the muscle area, the electrical activity is picked up and amplified by the EMG recorder as sound. The sound gets louder as the needle tip gets closer to and finally within the muscle. The needle is advanced behind the eye to the end of the muscle, about 3 cm, keeping the needle within the muscle, guided by the amplitude of the recorded sound. This is important, as the drug will anesthetize the nerves and the muscle with injection of the first few drops, thereafter leaving no guide as to position of the needle. The drug solution is injected starting at this deepest point, with continued injection of solution as the needle is withdrawn. In order to get the maximum effect, all the fibers of the muscle must be exposed to the drug. A smaller volume and concentration are applied when a sub-maximum effect is wanted. The muscle will be inactive for a day from the anesthetic effect of the drug. It gradually recovers from the myotoxic effect of the drug over the next week, and eye position and movement typically improve thereafter as the muscle enlarges and strengthens. (Scott, A. B., Alexander, D. E., Miller, J. M., 2007, Bupivacaine injection of eye muscles to treat strabismus. Br J. Opthalmol. 91 (2), 146-148)

EXAMPLE 2

Suppose the physician wants to strengthen a muscle of the forearm that controls extension of a finger scarred by a burn and restricted in its extension. Attempts to extend the finger activate the muscle, and the movement of the muscle is seen under the skin. Marks are put on the skin overlying the target muscle at intervals of about 1 cm to guide drug placement, realizing that EMG-recorded electrical activity will cease to be a guide to placement after the first few injections act to anesthetize the muscle. Injections of local anesthetic are placed into the muscle along its length. In a time sequence similar to Example 1, the enlarged and strengthened muscle gains enhanced power to move the damaged finger.

In one case of eye muscle injection, I marked the solution with a contrast agent to show the exact location of the injected drug. MRI scan images taken immediately after injection showed that most of the solution had been placed surrounding the muscle rather than having been deposited in the muscle. All the same, the muscle became larger and stronger. This teaches that exposure of the fibers can also be effected by injecting around the muscle to bathe it. All the muscle fibers must be exposed to the drug to provide the maximal effect. Reducing exposure of the muscle fibers to the drug by reducing the volume of solution injected or by using a lower concentration of drug can be expected to provide a lesser effect. Both amino-ester and amino amide local anesthetics have the property of causing muscle damage, but those of the amino-amide class are more powerful in this regard and are preferred; bupivacaine, ropivacaine, and etidocaine are examples of drugs of this class.

CONCLUSIONS, RAMIFICATIONS, AND SCOPE

I have thus described a method, many aspects of which can strengthen and improve the manner of treatment of conditions in which muscle function is inadequate. The eye muscle condition of strabismus ("crossed eyes") will be altered both by substitution of this simpler treatment for surgery, and by application of the muscle strengthening treatment in cases where surgery on the eye muscles is inappropriate. The method for strengthening muscles has advantages over surgical treatment in that a simple injection in the office suffices, with no need for expensive hospitalization and extended recovery. The material injected is an anesthetic, so that pain is minimal, and there is no pain following injection. The method has advantages over botulinum toxin injection in that the injected muscle will recover its action within 7-10 days, whereas botulinum toxin requires the muscle to be paralyzed at least a month to have a good and lasting effect. During this month, the patient is usually unable to use the paralyzed eye effectively. The method has been shown to have an effect lasting many months, whereas botulinum toxin often requires re-injection at frequent intervals.

While the above description contains many specificities, these should not be construed as limitations on the scope, but as exemplifications of some presently preferred embodiments. Many other ramifications and variations are possible within the teachings. For example, while the method had been discussed with reference to the eye and finger muscles, striated muscles with inadequate strength in all parts of the body are potentially susceptible to treatment. While bupivacaine is the drug most used because of it availability and demonstrated toxicity, other local anesthetic drugs, especially of the amino-amide class, such as ropivacaine and etidocaine may show equal or greater ability to stimulate muscle growth and strengthening. Basic laboratory work has shown that muscles with fast contracting fibers seem more susceptible to regeneration with hypertrophy than do muscle with slower contracting fibers. These sorts of muscles are located especially in the limbs, the orbits, and the larynx, but most muscles contain some of these fast contracting fibers and potentially can be beneficially affected by this method both for treatment of disorders and for enhancement of function. Beyond human use, application to domestic animals of all types is envisioned, both for treatment and to enhance function. Thus the scope should be determined by the appended claims and their legal equivalents, and not by the examples given.

I claim:

1. A method of strengthening a skeletal muscle by exposing the fibers of such a muscle to a concentration of a local anesthetic drug in sufficient quantity to effectively strengthen such muscle, said local anesthetic drug being applied to the fibers of said skeletal muscle with the purpose of strengthening said muscle to improve its function.

2. The method of claim 1 wherein such muscle fibers are selected from one of the eye muscles and exposed to the local anesthetic drug, bupivacaine, in a concentration of 0.25% to 5.0%, and in a volume of 1.0 ml to 7.0 ml by injection into such eye muscle, with the purpose of strengthening this muscle so that it puts greater tension on the eye and pulls it into an improved alignment.

3. The method of claim 1 wherein such muscle fibers are selected from one of the eye muscles and exposed to the local anesthetic drug, bupivacaine, in a concentration of 0.25% to 5.0%, and in a volume of 1.0 ml to 7.0 ml by placing the drug around such muscle, with the purpose of strengthening this muscle so that it puts greater tension on the eye and pulls it into an improved alignment.

4. The method of claim 1 wherein said local anesthetic drug is bupivacaine.

5. The method of claim 1 wherein said local anesthetic drug is placed around such a muscle in a sufficient amount to strengthening such muscle to improve its function.

6. The method of claim 5 wherein said local anesthetic drug is bupivacaine.

7. A method of strengthening a skeletal muscle, comprising:
   a. identifying and selecting a skeletal muscle that requires strengthening,
   b. exposing the fibers of such a muscle to a concentration of a local anesthetic drug in sufficient quantity to effectively strengthen such muscle.

8. The method of claim 7 wherein such muscle fibers are selected from one of the eye muscles and exposed to the local anesthetic drug, bupivacaine, in a concentration of 0.25% to 5.0%, and in a volume of 1.0 ml to 7.0 ml by injection into such eye muscle, with the purpose of strengthening this muscle so that it puts greater tension on the eye and pulls it into an improved agent.

9. The method of claim 7 wherein such muscle fibers are selected from one of the eye muscles and exposed to the local anesthetic drug, bupivacaine, in a concentration of 0.25% to 5.0%, and in a volume of 1.0 ml to 7.0 ml by placing the drug around such muscle, with the purpose of strengthening this muscle so that it puts greater tension on the eye and pulls it into an improved alignment.

* * * * *